(12) United States Patent
Murao et al.

(10) Patent No.: US 7,078,199 B2
(45) Date of Patent: Jul. 18, 2006

(54) METHOD OF MANUFACTURING COMPOUND WITH BIOCATALYST BY USING CONTROLLED REACTION TEMPERATURE

(75) Inventors: Kozo Murao, Kanagawa (JP); Katsuo Ishii, Kanagawa (JP); Hiroyasu Banba, Kanagawa (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 294 days.

(21) Appl. No.: 10/480,810

(22) PCT Filed: Jun. 20, 2002

(86) PCT No.: PCT/JP02/06163

§ 371 (c)(1),
(2), (4) Date: Dec. 22, 2003

(87) PCT Pub. No.: WO03/000914

PCT Pub. Date: Jan. 3, 2003

(65) Prior Publication Data

US 2004/0219647 A1   Nov. 4, 2004

(30) Foreign Application Priority Data

Jun. 22, 2001   (JP) .............................. 2001-189894

(51) Int. Cl.
*C12P 13/02* (2006.01)

(52) U.S. Cl. ..................................... 435/129

(58) Field of Classification Search ................ 435/129, 435/288.4, 294.1, 305.2, 819
See application file for complete search history.

(56) References Cited

U.S. PATENT DOCUMENTS

| 3,940,492 A | * | 2/1976 | Ehnstrom ..................... 426/16 |
| 4,248,968 A | | 2/1981 | Watanabe et al. |
| 6,849,432 B1 | * | 2/2005 | Abe et al. ................... 435/129 |

FOREIGN PATENT DOCUMENTS

| EP | 188316 | 7/1986 |
| EP | 1352 964 | 10/2003 |
| GB | 1 348 295 | 3/1974 |
| JP | 2001-17195 | 1/2001 |

OTHER PUBLICATIONS

Sun Ho Park, et al., "Optimization of Operating Temperature for Continuous Glucose Isomerase Reactor System", Biotechnology and Bioengineering, vol. 23, No. 6, XP-002298042, 1981, pp. 1237-1254.

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

Provided is a method for producing a compound using a biocatalyst. In the method for continuously producing a compound using a biocatalyst in one or a plurality of reaction tanks, the downstream reaction temperature is set higher than the upstream reaction temperature of the flow of the catalyst in a reaction tank or between reaction tanks.

18 Claims, No Drawings

METHOD OF MANUFACTURING COMPOUND WITH BIOCATALYST BY USING CONTROLLED REACTION TEMPERATURE

TECHNICAL FIELD

The present invention relates to a method for producing a compound using a biocatalyst.

BACKGROUND TECHNIQUE

Biocatalysts, such as cells, immobilized cells, or immobilized enzymes (these may be hereinafter referred to as "biocatalysts") have advantages in that, for example, reaction processes can be simplified, the reaction products have high purity due to a reduced amount of by-products generated, and highly-reactive materials can also be stably produced due to a mild reaction condition. Thus, biocatalysts are recently used in the production of many compounds.

Biocatalysts, however, cause lowering (deactivation) in the catalytic activity during a reaction. Therefore, methods for regulating the deactivation have been studied in order to enhance the amount of the compound produced per unit amount of catalyst, that is, the productivity of the catalyst (hereinafter, simply referred to as "productivity"). For example, those methods include: a method in which a reaction is carried out at low temperature from the freezing point to 15° C. (Japanese Patent Examined Publication (kokoku) No. 56-38118); a method in which low-concentrated substrates are continuously supplied through a plurality of feed hoppers (Japanese Patent Examined Publication (kokoku) No. 57-1234); a method in which microorganisms or a treated product thereof are processed with an organic solvent (Japanese Patent Application Laying-Open (kokai) No. 5-308980); a method in which a reaction is carried out in the presence of higher unsaturated fatty acids (Japanese Patent Application Laying-Open (kokai) No. 7-265090); and a method in which cells are cross-linked with glutaraldehyde or the like (Japanese Patent Application Laying-Open (kokai) Nos. 7-265091 and 8-154691).

DISCLOSURE OF THE INVENTION

These methods by themselves, however, do not sufficiently enhance the productivity of a catalyst and, as a result, the amount of the catalyst used in the production of a compound is not negligible. This results in not only the increased production cost of a compound but also the increased amount of disposable catalysts and, thus, a method for disposing thereof becomes a concern.

Accordingly, the object of the present invention is to provide a method for producing a compound in a cost-effective, efficient, and environmentally-friendly manner, which more effectively utilizes a biocatalyst by improving a productivity of a catalyst, thereby lowering a proportional cost of a catalyst in the production of a compound and generating less waste.

In general, a reaction is preferably carried out at lower temperature in order to prevent the deactivation when producing a compound using a biocatalyst. However, the present inventors have conducted concentrated studies and, as a result, found that the productivity of the catalyst was improved by raising a downstream temperature than the upstream temperature of the flow of the catalyst in a reaction tank. This has led to the completion of the present invention.

Further, they have found that the present invention could be attained by a technically and economically simple manner, that is, a decrease in the amount of heat removed from the reaction tank is sufficient when the reaction is an exothermic reaction.

More specifically, the present invention is as follows:

(1) A method for continuously producing a compound using a biocatalyst in one or a plurality of reaction tanks, wherein a downstream reaction temperature is set higher than a upstream reaction temperature in a reaction tank or between reaction tanks;

(2) The production method according to (1), wherein the downstream reaction temperature is set higher than the upstream reaction temperature by at least 1° C. in a reaction tank or between reaction tanks;

(3) The production method according to (1), wherein the downstream reaction temperature is set higher than the upstream reaction temperature by at least 5° C. in a reaction tank or between reaction tanks;

(4) The method for producing a compound according to any one of (1) to (3), wherein the biocatalyst is microbial cells or a processed product thereof;

(5) The method for producing a compound according to (4), wherein the compound to be produced is an amide compound;

(6) The method for producing a compound according to (5), wherein the compound to be produced is acrylamide, nicotinamide, or 5-cyanovaleramide; and (7) The method for producing a compound according to any one of (1) to (6), wherein the catalyst flows in parallel with the flow of the reaction solution in the reaction tank.

The present invention will be described in more detail below.

The present invention is applied to a method for continuously producing a compound in a reaction tank using a biocatalyst. A method for continuously producing a compound in a reaction tank using a biocatalyst refers to a method for producing a compound using a bioreactor including a biochemical reactor (an enzyme reactor) and a biological reactor (a microbiological reactor) and can be carried out using various types of reactors such as a reactor of stirred tank type, fixed bed type, fluidized bed type, or moving bed type. In this method, the reaction for producing a compound is carried out in a reaction tank. Some reactions utilize only one reaction tank and some other reactions utilize a plurality of reaction tanks. Preferably, two or more reaction tanks are utilized from the viewpoints of, for example, the improvement in the operability such as temperature control and an easiness of catalyst substitution and the improvement in the reaction efficiency.

The biocatalysts used in the present invention include animal cells, plant cells, organelles, cells (viable cells or killed cells) containing an enzyme which catalyzes the reaction of interest, or a processed product thereof. The processed product includes a crude or refined enzyme extracted from cells, and an immobilized product of animal cells, plant cells, organelles, cells (viable cells or killed cells), or enzymes per se by, for example, an entrapping method, a cross-linking method, or a carrier binding method. Cells used as biocatalysts include microbial cells such as *Rhodococcus rhodochrous* and *Pseudomonas chlororaphis* and, as the enzyme, nitrile-hydratase produced from these microorganisms is included. The "entrapping method" used herein is a method in which cells or enzymes are enveloped into fine lattices of polymer gels or covered with a semipermeable polymeric coat. The "cross-linking method" is a method in which an enzyme is cross-linked with a reagent having two or more functional groups (a polyfunctional cross-linking agent). The "carrier binding method" is a method in which an enzyme is bound to a water-insoluble carrier. Immobilizing carriers used in the immobilization include glass beads, silica gel, polyurethane, polyacrylamide, polyvinyl alcohol, carrageenan, alginic acid, agar, and gelatin.

The entrapping-immobilization method is widely applied to the industrial use among methods for immobilizing cells because it can provide immobilized cells having high cell concentration. For example, Japanese Patent Examined Publication (kokoku) No. 58-35078 and Japanese Patent Application Laying-Open (kokai) No. 7-203964 disclose an example in which an acrylamide and/or an acrylamide derivative are used as a monomer for entrapping-immobilization. The compound produced according to the present invention is not particularly limited as long as the compound can be produced by a biocatalytic action. Examples of compounds include general-purpose chemicals such as alcohols and amides, and foods, perfumeries, and medicines such as amino acid, antibiotics, and physiological substances or a raw material or intermediate product thereof. In particular, in the production of general-purpose chemicals, it is important and indispensable to decrease the amount of catalysts used from the economical point of view. Thus, the present invention is preferred in the production of general-purpose chemicals using biocatalysts and, more specifically, is more preferred in the production of amide compounds, which are general-purpose chemicals recently mass-produced using biocatalysts. Examples of amide compounds include acrylamide, nicotinamide, and 5-cyanovaleramide.

The method for continuously producing a compound according to the present invention is a method in which a starting compound is continuously or intermittently added to a reaction tank while continuously or intermittently removing a reaction solution therefrom without removing the total amount of the reaction solution from the reaction tank. Specifically, it does not refer to the production in which the total amount of the reaction solution is periodically removed, i.e., the production that is called a batch reaction or semibatch reaction. Possible reaction modes for continuously producing a compound using a biocatalyst according to the present invention include a mode which utilizes a fixed-bed, moving-bed, fluidized-bed, stirred tank and the like. In any of these modes, the reaction tank used in the present invention is preferably equipped with a cooling or heating system such as a jacket, a cooling or heating coil, an external cyclic cooling system or external cyclic heating system. Alternatively, the reactor as a whole or a part thereof may be immersed in a constant-temperature bath to realize cooling or heating. A heat exchanger can also be inserted between reaction tanks.

In such a mode, a biocatalyst is deactivated over the elapse of the time in any case. Thus, the biocatalyst should be continuously or intermittently added to a reaction tank while being removed from the reaction tank. Therefore, in the continuous production method, a given flow of the biocatalyst from an upstream toward a downstream is generated. The "upstream" according to the present invention refers to a side to which catalysts are added to a reaction tank and, conversely, the "downstream" refers to a side from which the catalysts are removed.

Each reaction mode will be described in more detail. In the case of a fixed bed, it is supposed that a fixed bed comprising a plurality of tanks should be used as a pseudo-moving bed (used in a merry-go-round system), and in the case of a fluidized bed or a stirred tank, it should be a series of plural tanks. In this case, the upstream reaction tank is a reaction tank which is located on the side to which catalysts are added among a plurality of reaction tanks, and the downstream reaction tank is a reaction tank which is located on the side from which catalysts in the reaction system are removed. In the case of a moving bed in which a biocatalyst moves along with the flow of a reaction solution in one reaction tank, the "upstream" refers to a vicinity of what is called an inlet of a reaction tank to which catalysts are added, and the "downstream" refers to a vicinity of what is called an outlet of a reaction tank from which catalysts in the reaction system are removed. The "moving bed" used herein includes the reaction mode utilizing a flow tubular reaction tank.

Accordingly, "the downstream reaction temperature is set higher than the upstream reaction temperature of the flow of the catalyst in the reaction tank" means that the downstream reaction temperature is set higher than the upstream reaction temperature of the above-described catalyst. More specifically, in a serial mode utilizing a plurality of tanks, the temperature of the reaction tank located at the lowermost stream among a plurality of tanks is set higher than the temperature of the reaction tank located at the uppermost stream. For example, when four reaction tanks are connected, the temperature of the fourth reaction tank is set higher than that of the first tank. In a serial mode utilizing a single tank such as a moving bed, the temperature of the portion near the outlet of the reaction tank is set higher than the temperature of the portion near the inlet of the reaction tank. The phrase "the reaction temperature is higher" used herein means that the temperature can be confirmed to be higher in a measurable range, i.e., higher by at least 0.1° C. In order to make the present invention more effective, the temperature is preferably higher by at least 1° C., and is more preferably higher by at least 5° C. The reaction temperature is adequately selected taking the stability of the catalyst used in the reaction and the like into consideration.

In the present invention, the flow of a catalyst is preferably in parallel with the flow of a reaction solution. The flow of a catalyst is in parallel with the flow of a reaction solution means that the flow of the reaction solution is toward the same direction as the flow of the catalyst. When the reaction is an exothermic reaction if the catalyst flows in the same direction as the reaction solution, any regulation of the amount of heat removed is sufficient for raising the reaction temperature and, thus, the downstream reaction temperature can be easily set higher than the upstream reaction temperature of the flow of the catalyst in the reaction tank.

BEST MODE FOR CARRYING OUT THE INVENTION

The present invention will be described in more detail with reference to the following examples. These examples, however, are not intended to limit the technical scope of the present invention.

EXAMPLE 1

(1) Preparation of Biocatalyst

*Rhodococcus rhodochrous* J1 strain having an activity of nitrile-hydratase (deposited with the International Patent Organism Depositary of the National Institute of Advanced Industrial Science and Technology as of Sep. 18, 1987 under the accession number FERM BP-1478 (Tsukuba Central 6, 1-1-1 Higashi, Tsukuba, Ibaraki, Japan)) was aerobically cultured in a medium (pH 7.0) containing 2% of glucose, 1% of urea, 0.5% of peptone, 0.3% of yeast extract, and 0.05% of cobalt chloride (all values are by mass) at 30° C. The cultured product was harvested using a centrifuge and washed with 50 mM phosphate buffer (pH 7.0) to obtain a cell suspension (15% by mass of dry cell).

(2) Reaction from 3-cyanopyridine to Nicotinamide

Four jacketed separable flasks (interior volume of 1 L) were connected in series. To the first tank were continuously added 50 mM phosphate buffer (pH 8) having 15% 3-cyanopyridine dissolved therein at a flow rate of 200 ml/hr and a cell suspension at a flow rate of 0.3 ml/hr and, while stirring, a reaction was carried out while regulating the reaction temperature using coolant (20° C.) of the jacket so as to bring the temperatures of the first to the fourth reaction tanks to 30° C., 30° C., 32° C., and 35° C., respectively.

Three days later, the reaction solution discharged from the fourth tank was assayed by liquid chromatography (column: ODS-80A (GL Sciences Inc., eluant: a 5% acetonitrile/10 mM phosphate buffer (pH 7), detection: 200 nm)). As a result, 3-cyanopyridine was not detected while about 17% nicotinamide was detected.

Comparative Example 1

A reaction was carried out using the cell suspension prepared in Example 1 in the same manner as used in Example 1, except that the reaction temperature was set at 30° C. for all of four tanks.

Three days later, the reaction solution discharged from the fourth tank was assayed in the same manner by liquid chromatography. As a result, only 16% of nicotinamide was generated and about 1% of unreacted 3-cyanopyridine was detected.

Comparative Example 2

A reaction was carried out using the cell suspension prepared in Example 1 in the same manner as used in Example 1, except that the reaction temperature was set at 35° C. for all of four tanks.

Three days later, the reaction solution discharged from the fourth tank was assayed in the same manner by liquid chromatography. As a result, only 15% of nicotinamide was generated and about 2% of unreacted 3-cyanopyridine was detected.

EXAMPLE 2

(1) Preparation of Biocatalyst

*Pseudomonas chlororaphis* B23 having an activity of nitrile-hydratase (deposited with the International Patent Organism Depositary of the National Institute of Advanced Industrial Science and Technology as of Nov. 16, 1981 under the accession number FERM BP-187 (Tsukuba Central 6, 1-1-1 Higashi, Tsukuba, Ibaraki, Japan)) was aerobically cultured in a medium (pH 7.5) containing 1.0% of sucrose, 0.5% of methacrylonitrile, 0.3% of peptone, 0.1% potassium dihydrogenphosphate, 0.1% dipotassium hydrogenphosphate, 0.1% of magnesium sulfate, 0.3% of yeast extract, and 0.001% of ferrous sulfate (all values are by mass) at 25° C. The cultured product was washed with 50 mM phosphate buffer (pH 7.0) to obtain a cell suspension (12% by mass of dry cell).

Separately, an aqueous solution of monomer mixture was prepared so as to bring acrylamide, methylenebisacrylamide, and 2-dimethylaminopropyl methacrylamide to 30, 1, and 4% by mass, respectively.

Subsequently, a cell suspension, an aqueous monomer solution, and an aqueous 10% by mass N,N,N',N'-tetramethyl ethylene diamine solution were successively subjected to line mixing with an aqueous 10% by mass ammonium persulfate solution at 5, 2, 0.1, and 0.1 L/hr, respectively, for polymerization. Thereafter, the resultant product was cut into about 1 mm-square particles to obtain immobilized cell particles. These immobilized cell particles were washed with 50 mM phosphate buffer (pH 7.0) by dipping while being fluidized to obtain immobilized cell catalysts (about 8% by mass of dry cell is contained in this catalyst).

(2) Reaction from Acrylonitrile to Acrylamide Using Immobilized Cell Catalyst.

A similar device as used in Example 1 was provided, except that wire gauzes were provided at the outlets of the reaction solution from each reaction tank to prevent the immobilized cell catalysts from being discharged from each reaction tank. 50 g of immobilized cell catalyst was added to each reaction tank. 50 mM phosphate buffer (pH 7) and acrylonitrile were continuously added to the first tank at 155 ml/hr and at 25 g/hr, respectively. Only acrylonitrile was continuously added to the second tank at 20 g/hr. While stirring in each of these tanks, the reaction temperature was regulated using coolant (5° C.) of the jacket so as to bring the temperature of the first to the fourth reaction tanks to 10° C., 10° C., 12° C., and 15° C., respectively. 6 g of catalyst was removed from the fourth tank once a day using wire gauzes for substituting catalysts in the reaction tank. 6 g each of catalyst was transferred from the third tank to the fourth tank, from the second tank to the third tank, and from the first tank to the second tank, and 6 g of catalyst was then added to the first tank, thereby continuously performing the acrylamide-producing reaction.

The reaction solution discharged from the fourth tank was assayed by gas chromatography (column: PraPak-PS (Waters), 1 m, 180° C., carrier gas: nitrogen, detector: FID) once a day. During the operation for about three months, only about 30% of acrylamide was detected while no unreacted acrylonitrile was detected.

Comparative Example 3

A reaction was carried out using the immobilized cell catalyst prepared in Example 2 in the same manner as used in Example 2, except that the reaction temperature was set at 10° C. for all of four tanks.

After about 1.5 months, unreacted acrylonitrile began to remain in the reaction solution discharged from the fourth tank, and the quality of the acrylamide product began to deteriorate. The amounts of catalysts added and removed were changed to 8 g per day, and as a result, unreacted acrylonitrile came to be not detected again.

INDUSTRIAL APPLICABILITY

The present invention can easily decrease the amount of the biocatalyst used in the production of a compound and, thus, can provide a method for producing a compound in a cost-effective, efficient, and environmentally-friendly manner, which is capable of lowering the proportional cost of a catalyst in the production of a compound and generating less wastes.

All publications cited herein are incorporated herein in their entirety. A person who has ordinary skill in the art would easily understand that various changes and modifications of the present invention are possible without departing from the range of the technical idea and the scope of the invention described in the accompanying claims. The present invention is also intended to include such changes and modifications.

The invention claimed is:

1. A method for continuously producing an amide compound in the presence of a biocatalyst in two or more reaction tanks, wherein a downstream reaction temperature is set higher than an upstream reaction temperature by at least 1° C. between reaction tanks.

2. The method according to claim 1, wherein the downstream reaction temperature is set higher than the upstream reaction temperature by at least 5° C. between reaction tanks.

3. The method according to claim 1, wherein the biocatalyst is microbial cells or a processed product thereof.

4. The method according to claim 1, wherein the compound produced is acrylamide, nicotinamide, or 5-cyanovaleramide.

5. The method according claim 1, wherein the biocatalyst flows in parallel with a flow of reaction solution in the reaction tanks.

6. The method according to claim 2, wherein the biocatalyst is microbial cells or a processed product thereof.

7. The method according to claim 3, wherein the biocatalyst is microbial cells.

8. The method according to claim 4, wherein the biocatalyst is microbial cells or a processed product thereof.

9. The method according to claim 5, wherein the biocatalyst is microbial cells or processed product thereof.

10. The method according claim 2, wherein the biocatalyst flows in parallel with a flow of reaction solution in the reaction tanks.

11. The method according claim 3, wherein the biocatalyst flows in parallel with a flow of reaction solution in the reaction tanks.

12. The method according claim 4, wherein the biocatalyst flows in parallel with a flow of reaction solution in the reaction tanks.

13. The method according claim 5, wherein the biocatalyst flows in parallel with a flow of reaction solution in the reaction tanks, and wherein said biocatalyst is a processed product of microbial cells.

14. The method according claim 6, wherein the biocatalyst flows in parallel with a flow of reaction solution in the reaction tanks.

15. The method according claim 7, wherein the biocatalyst flows in parallel with a flow of reaction solution in the reaction tanks.

16. The method according claim 8, wherein the biocatalyst flows in parallel with a flow of reaction solution in the reaction tanks.

17. The method according claim 9, wherein the biocatalyst flows in parallel with a flow of reaction solution in the reaction tanks.

18. The method of claim 1, wherein the amide compound is acrylamide.

* * * * *